United States Patent [19]
Chou et al.

[11] Patent Number: 6,162,541
[45] Date of Patent: *Dec. 19, 2000

[54] SUPERABSORBING COMPOSITIONS AND PROCESSES FOR PREPARING SAME

[75] Inventors: Yueting Chou, Chesterfield; Timothy Paul Feast, Wildwood; Jingen Zhang, Maryland Heights, all of Mo.

[73] Assignee: Solutia Inc., St Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 09/192,386

[22] Filed: Nov. 16, 1998

Related U.S. Application Data

[60] Provisional application No. 60/065,670, Nov. 18, 1997.

[51] Int. Cl.⁷ .................................................. D02G 3/00
[52] U.S. Cl. ...................... 428/376; 427/213.33; 427/222; 427/389.9; 427/391; 427/392; 427/394; 427/395; 427/396; 428/316; 428/378; 428/393; 428/395; 428/396; 521/84.1; 521/315; 521/322; 521/363

[58] Field of Search ....................... 428/376, 316, 428/378, 393, 395, 396; 427/213.33, 222, 389.9, 391, 392, 394, 395, 396; 521/84.1; 528/315, 322, 363

[56] References Cited

U.S. PATENT DOCUMENTS

| | | |
|---|---|---|
| 5,889,072 | 2/2000 | Chou et al. .......................... 521/84.1 |
| 6,027,804 | 2/2000 | Chou et al. .......................... 521/84.1 |

*Primary Examiner*—Morton Foelak
*Attorney, Agent, or Firm*—Gordon F. Sieckmann; Thompson Coburn LLP

[57] ABSTRACT

Superabsorbent polymer compositions comprising a fiber-containing composition derived from cellulosic fibers, synthetic fibers or mixtures thereof which is at least partially coated with a partially acidified, hydrolyzed, internally plasticized, crosslinked, superabsorbing polymers derived from polysuccinimide and processes for preparing same.

34 Claims, No Drawings

SUPERABSORBING COMPOSITIONS AND PROCESSES FOR PREPARING SAME

This application claims the benefit of priority under 35 U.S.C. § 119(e) of U.S. Provisional Application No. 60/065,670 filed Nov. 18, 1997.

BACKGROUND OF THE INVENTION

This invention relates to compositions containing superabsorbing polymers based on L-aspartic acid and to process (es) for preparing such compositions.

Polysuccinimide (PSI) is prepared by thermal polycondensation of L-aspartic acid which can then be base-hydrolyzed to polyaspartate salt which has many industrial uses such as lubricant in metalworking fluids. Crosslinking PSI before or after hydrolysis renders the hydrolyzed salt superabsorbent in that it can absorb many times its weight of liquid such as water. This capability of absorbing significant quantities of fluids, including body exudates and aqueous compositions of all kinds, creates another important class of application for these polymers in products such as diapers, sanitary napkins, incontinence products, towels, tissues and the like. These superabsorbing polymers are in the prior art as typically disclosed in U.S. Pat. No. 5,461,085 (Nagatomo et al); U.S. Pat. No. 5,525,703 (Kalota) and U.S. Pat. No. 5,612,384 (Ross et al). Though articles of superabsorbing polymers derived from L-aspartic acid are recognized in this art as desirable, to date they are only disclosed in unshaped, particulate form as recovered from the hydrolysis step forming the salt. Note all the examples of the patents referenced above.

The absorbent body of many absorbent articles, such as diapers, sanitary napkins, incontinence products, etc., are normally comprised of one or more layers of cellulose fluff pulp, which may be intermixed with superabsorbent polymers. Since the superabsorbing polymers derived from L-aspartic acid to date are only disclosed in unshaped, particulate form, the problem exists of preventing migration of the superabsorbent polymer particles within the layers of pulp fibers.

In view of the noted applications, it would be highly desirable to provide biodegradable superabsorbent polymers derived from L-aspartic acid in compositions to facilitate formation into products such as diapers and the like. It would also be highly desirable to provide superabsorbent polymer compositions avoid the migration problem.

The superabsorbent compositions of the present invention provide a solution to many problems encountered with unshaped, particulate superabsorbent polymers derived from L-aspartic acid. For example, the superabsorbent compositions of the invention have the advantage of avoiding the problem of migration by being bound to the pulp fibers. The superabsorbent polymer component of the compositions of the invention are also biodegradable.

SUMMARY OF THE INVENTION

Now, significant developments have been made in producing compositions containing superabsorbent polymers derived from L-aspartic acid.

Accordingly, a principal object of this invention is to produce synthetic, superabsorbent compositions containing superabsorbent polymers of L-aspartic acid derivatives.

Another object is to provide a method for producing such compositions.

A further object is to provide an intermediate precursor for contacting with fiber-containing compositions which can be converted into superabsorbent polymer upon crosslinking of the intermediate precursor.

Other objects will in part be obvious and will in part appear from the following detailed description.

These and other objects are accomplished by the following multiple aspects of the invention.

In one aspect of the invention, an uncrosslinked, non-hydrolyzed, internally plasticized poly(imide-co-amide) intermediate precursor is produced which is useful in later forming such superabsorbing polymer compositions. The intermediate is prepared by reacting a regulated amount of about 1 to about 20% of succinimide groups of the PSI with a minor, internally plasticizing amount of one or more monoamine compounds, such as diethanolamine. The partial amidation with the monoamine compound softens the polymer and facilitates subsequent drawing into fiber form or forming into film. For example, the poly(imide-co-amide) intermediate produced using diethanolamine as the monoamine compound has repeating structural units represented by formula (1)

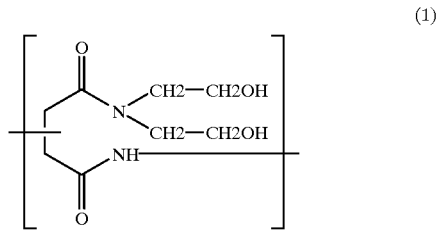

and repeating structural units represented by formula (2)

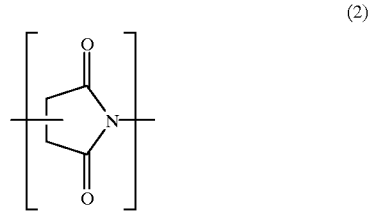

the mole fraction of repeating structural units represented by the formula (1) being about 0.01 to about 0.20.

The internally plasticized poly(imide-co-amide) intermediate is subsequently hydrolyzed to convert essentially all of the succinimide groups into aspartate groups. A portion of the aspartate groups in the polyamide produced as a result of the hydrolysis are then partially acidified to produce a partially acidified, hydrolyzed, internally plasticized polysuccinimide composition.

In another aspect of the invention, a crosslinking agent is incorporated into the partially acidified, hydrolyzed, internally plasticized polysuccinimide composition to form a crosslinkable but uncrosslinked intermediate composition before contacting with the fiber-containing composition. Crosslinking aspartate groups of the polymer occurs after contacting the intermediate precursor with the fiber-containing composition in an after-treating, drying or curing step by subjecting the intermediate precursor to crosslinking conditions to render the polymer capable of superabsorbing. Premature crosslinking is minimized or avoided by incorporating heat reactive crosslinking agents into the composition at low temperature, i.e. from or about 0° C. to or about 25° C.

In yet another aspect of the invention, the products of the process differ from those previously known in that fiber-containing compositions are at least partially coated with the superabsorbing polymer. The crosslinked superabsorbing polymers are polyamide containing at least three divalent or polyvalent moieties randomly distributed along the polymer chain having the following formulas:

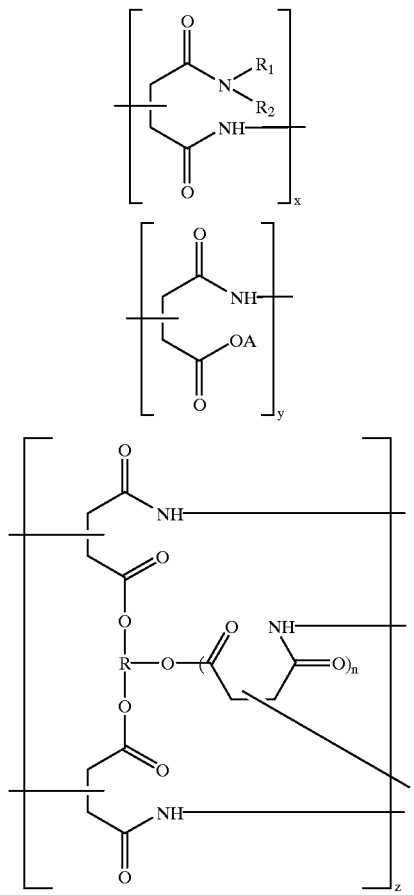

where A represents hydrogen, alkali metal cation, ammonium, quaternary ammonium or mixtures thereof, R represents a divalent or polyvalent crosslinker moiety, x, y and z represent mole fractions of the moieties in the polyamide and are respectively about 0.01 to 0.20; about 0.40 to 0.90 and about 0.01 to 0.50 wherein the sum of x, y and z is 1.0, and n is an integer from 0 to 4. $R_1$ and $R_2$ are substituents on the monoamine compound used for the internal plasticization of PSI and can be the same or different. Optionally, the superabsorbent polymer contains minor amounts of unreacted succinimide repeating units, i.e. repeating unit disclosed in formula (2) above, and unreacted acidified aspartate repeating units, i.e. repeating unit disclosed in formula (4) herein. As used herein, a minor amount of succinimide repeating units or acidified aspartate repeating units is an amount up to that amount which has a detrimental effect on the absorbency properties of the superabsorbent polymer.

DETAILED DESCRIPTION OF THE INVENTION

In one embodiment, this invention relates to a process for preparing a superabsorbing polyamide composition comprising i) contacting a fiber-containing composition derived from cellulosic fibers, synthetic fibers or mixtures thereof with a solution of a crosslinkable, uncrosslinked, partially acidified, hydrolyzed, internally plasticized polysuccinimide (PSI) composition to produce an at least partially coated fiber-containing composition, and ii) heating the at least partially coated fiber-containing composition under crosslinking conditions to crosslink a portion of uncrosslinked aspartate groups in the PSI composition and form the superabsorbing polyamide composition.

In another embodiment, this invention further relates to a process for preparing a superabsorbing polyamide composition comprising i) contacting a dewatered cellulose pulp with a solution of a crosslinkable, uncrosslinked, partially acidified, hydrolyzed, internally plasticized polysuccinimide (PSI) composition to produce an at least partially coated cellulose pulp composition, and ii) drying said at least partially coated cellulose pulp composition under crosslinking conditions to crosslink a portion of uncrosslinked aspartate groups in said PSI composition and form the superabsorbing polyamide composition.

In yet another embodiment, this invention relates to a superabsorbing polymer composition comprising a fiber-containing composition derived from cellulosic fibers, synthetic fibers or mixtures thereof which is at least partially coated with a partially acidified, hydrolyzed, internally plasticized, crosslinked, superabsorbing polymer derived from polysuccinimide.

As used herein, "fiber-containing compositions" mean fibers or materials prepared from or containing the fibers, e.g. mats, webs, sheets, nonwoven matrices and the like. The synthetic fibers include, but are not limited to, polyesters, copolymers of polyesters and polyamides, polyvinyl alcohol, polypropylene, polyamides, copolymers of isobutylene and maleic anhydride or mixtures thereof. The currently preferred fiber-containing compositions are selected from cellulose pulp, cellulose fluff or materials derived from same.

Cellulosic fibers of diverse natural origin are applicable to the invention. Digested fibers from softwood, hardwood or cotton linters are preferably utilized. The optimum cellulosic fiber source utilized in conjunction with this invention will depend upon the particular end use contemplated. Generally wood pulps will be utilized. Details of the production of wood pulp fibers are well known to those skilled in the art. Applicable wood pulps include, chemical pulps and mechanical pulps. Chemical pulps are currently preferred. Completely bleached, partially bleached and unbleached fibers are applicable. Examples of cellulosic or cellulose-type fiber include pulp fibers, pulp fluff, cotton fibers and cellulose type chemical fiber (or chemically modified cellulose), such as viscose rayon and acetate rayon or cellulose acetate. Fluff is pulped wood fibers provided in a highly individualized, i.e. disintegrated, state. The cellulosic fibers may be in the form of a cellulosic web, sheet or nonwoven, or loose cellulose fibers.

Synthetic superabsorbing polymers of the invention are derived from L-aspartic acid starting monomer available commercially from Solutia Inc.. L-aspartic acid is conventionally condensation polymerized in the presence of catalyst such as phosphoric acid. Processes for preparing homopolymer polysuccinimide (PSI) are described in U.S. Pat. Nos. 5,057,597; 5,315,010 and 5,319,145. Molecular weight (weight average $M_W$) is preferably at least 20,000 and more preferably at least 30,000 up to or about 100,000 Daltons. Such relatively high molecular weight is achieved by driving the polycondensation reaction to as complete a level as commercially feasible using catalyst concentrations, reaction temperature and time at the high end of the ranges disclosed in these patents. Water of condensation is removed as it is formed as taught in U.S. Pat. No. 5,484,945 (Nagatomo et al) the disclosure in which is incorporated herein by reference. In a preferred procedure, polycondensation is conducted at reduced pressure and 180° C. in the presence of 85% phosphoric acid as described in U.S. Pat. No. 5,142,062 (Knebel et al) the disclosure of which is also incorporated herein by reference. Succinimide ("S") groups of formula (2) are the repeating structural unit.

The S groups of the PSI are next ring-opening reacted with one or more monoamine compounds having the formula $HNR_1R_2$ in an amount functionally effective to internally plasticize the PSI and form a poly(imide-co-amide) intermediate. $R_1$ represents a hydrogen atom or an alkyl or alkenyl group of 1 to 55 carbon atoms, preferably 1–30, which can be straight chain or branched and unsubstituted or substituted, and $R_2$ represents a hydrogen atom, —OH, an alkyl or alkenyl group of 1 to 55 carbon atoms, preferably 1–30, which can be straight chain or branched and unsubstituted or substituted. The alkyl or alkenyl groups of $R_1$ and $R_2$ optionally contain one or more oxygen atoms. Optional substituents of the alkyl or alkenyl groups of $R_1$ and $R_2$ are common organic functional groups not interfering with the hydrolysis, acidification or crosslinking reactions of the invention such as one of the following: hydroxyl (—OH), ether (—$OR_3$), chloride (—Cl) and ketone (—$COR_3$), wherein $R_3$ represents an alkyl or alkenyl group of 1 to 8 carbon atoms. Currently preferred substituents of the invention are —OH and —$OR_3$.

The amount of monoamine compound in the poly(imide-co-amide) is that amount necessary to achieve adequate internal plasticization of the PSI and varies with the specific monoamine chosen. The amount of monoamine necessary is readily determined by one of ordinary skill and is based on the properties of the specific monoamine, e.g. molecular weight. Using diethanolamine as the monoamine, the repeating structural unit is represented by formula (1) in combination with S groups of formula (2), the mole fraction of repeating structural units represented by formula (1) being about 0.01 to about 0.20. Any compound containing one functional amino group which is reactable with PSI can be used to form the poly(imide-co-amide) intermediate and provide the internal plasticizing function. Compounds with two or more reactable amino groups tend to lead to crosslinking and therefore should be avoided. Other monoamino compounds interchangeably usable with the diethanolamine include, but are not limited to, methylamine, ethylamine, propylamine, butylamine, pentylamine, hexylamine, O-(2-Aminopropyl)-O'-(2-methoxyethyl) polypropylene glycol 500 (Jeffamine® M-600), ethanolamine, neopentanolamine, 3-isononyloxypropylamine, 3-propanolamine, 2-methoxyethylamine, 3-methoxy-propylamine, 3-ethoxypropyl-amine, ethylhexoxy-propylamine, isopropanolamine, and diisopropanol-amine. Monoamine is reacted with PSI in a solvent mixture at a temperature adequate for succinimide ring-opening which is typically about 40 to 70° C. Suitable solvents for the succinimide ring-opening reaction are water, polar organic solvents such as dimethylformamide (DMF), dimethylsulfoxide, and N-methyl-2-pyrrolidone (NMP), and non-polar organic solvents such as toluene and hexane. The preferred solvents for the succinimide ring-opening reaction are water and polar organic solvents, with water being the most preferred solvent. Using diethanolamine the reaction is illustrated as follows:

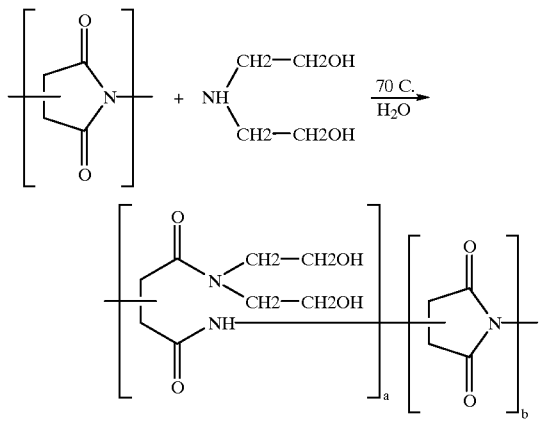

wherein a and b represent the mole fractions of the respective repeating structural units, and a is 0.01 to 0.20 and b is 0.99 to 0.80.

Internally plasticized PSI or poly(imide-co-amide) is next hydrolyzed with a regulated amount of base sufficient to form salt from essentially all of the S groups of the poly (imide-co-amide) to form an internally plasticized polyamide. As used herein, the term "essentially all" means > about 99%. The repeating unit of hydrolyzed succinimide, i.e. aspartate, has the following structure:

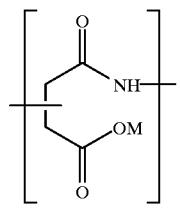

where M is an alkali metal cation such as $Na^+$, $K^+$, $Li^+$, ammonium or quaternary ammonium. This hydrolysis is accomplished by reacting the poly(imide-co-amide) reaction product of the prior process step with a suitable base, e.g. alkali metal hydroxide, ammonium hydroxide, and the like, in a suitable solvent selected from water, polar organic solvents such as DMF, DMSO and NMP, non-polar organic solvents such as toluene and hexane, and mixtures thereof. The currently preferred solvent is water and the currently preferred base is sodium hydroxide. In a preferred embodiment, this hydrolysis is conveniently accomplished by adding aqueous base solution in situ to the poly(imide-co-amide) reaction product of the prior process step. In the preferred embodiment, the hydrolyzed, internally plasticized PSI composition is totally dissolved in water solution after completion of the hydrolysis. Hydrolysis occurs at room temperature or, to reduce reaction time at elevated hydrolysis temperature typically up to about 75° C., until essentially all of the S groups are hydrolyzed.

The hydrolyzed, internally plasticized PSI composition, i.e. the internally plasticized polyamide, is next partially acidified with a regulated amount of an acid sufficient to convert about 1 to 50% of the aspartate groups into the acid form, i.e. acidified aspartate groups, for use in the crosslinking reaction. The amount of acid to partially acidify the hydrolyzed, internally plasticized polyamide is that amount necessary to reduce the pH to less than about 6.5, preferably from about 4 to about 6. The repeating unit of acidified aspartate has the following structure:

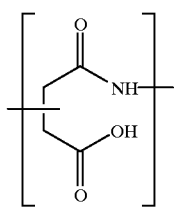

This partial acidification is accomplished by reacting the internally plasticized polyamide reaction product of the prior process step with a suitable acid in a suitable solvent selected from water, polar organic solvents such as DMF, DMSO and NMP, non-polar organic solvents such as toluene and hexane, and mixtures thereof. Suitable acids are acids that are capable of achieving a pH of less than 5 in the partial acidification reaction mixture and include mineral acids, e.g. hydrochloric acid, nitric acid, sulfuric acid, phosphoric acid and the like, and organic acids, e.g. carboxylic acids. The currently preferred solvent is water and the currently preferred acid is hydrochloric acid.

Crosslinker for eventually crosslinking acidified or non-acidified aspartate groups is then admixed under non-crosslinking conditions into the solution of partially acidified, hydrolyzed, internally plasticized PSI to form a crosslinkable, uncrosslinked, partially acidified, hydrolyzed, internally plasticized, PSI composition. The crosslinker can be admixed with the solution of partially acidified, hydrolyzed, internally plasticized PSI before or after concentration of the solution. In the preferred embodiment, crosslinker is admixed under non-crosslinking conditions into an aqueous solution of partially acidified, hydrolyzed, internally plasticized PSI to form a crosslinkable, uncrosslinked, partially acidified, hydrolyzed, internally plasticized PSI composition. According to the invention, crosslinking is delayed until after contacting with the fiber-containing composition, but crosslinker is added before contacting with the fiber-containing composition to insure that the crosslinker is evenly distributed throughout the partially acidified, hydrolyzed, internally plasticized PSI solution. Adding crosslinker to the solution while minimizing or avoiding crosslinking is accomplished by doing so at or about room temperature (22–25° C.) down to or about 0° C. This relatively low temperature protects against premature crosslinking before contacting with the fiber-containing composition and can vary with the crosslinking activity, or reactivity, of the crosslinker. Such non-crosslinking temperature conditions are chosen to avoid significant development of gel which occurs when crosslinked polyaspartate salt absorbs solvent, e.g. water, from the solution.

Suitable crosslinkers for the partially acidified, hydrolyzed, internally plasticized PSI composition according to the invention are any suitable polyfunctional compound having two or more functional groups that will react with the carboxylate groups of at least two of the aspartate groups at the pH conditions of the crosslinking reaction. Suitable crosslinkers include, but are not limited to, polyepoxides, haloepoxides (particularly chloroepoxides such as epichlorohydrin), polyaziridines, polyoxazolines, and mixtures thereof. As used herein, polyepoxides include compounds having two or more epoxide groups, e.g. diepoxides, triepoxides, and tetraepoxides. As used herein, haloepoxides include compounds having two or more functional groups wherein at least one functional group is an epoxide group and at least one functional group is a halogen. As used herein, polyaziridines include compounds having two or more aziridine groups and polyoxazolines include compounds having two or more oxazoline groups. Suitable polyepoxide crosslinkers of the invention include, but are not limited to, those represented by the formula:

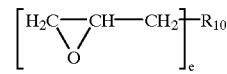

wherein "e" is 2 to 6, and $R_{10}$ is selected from a linear or branched aliphatic radical having 2 to 30 carbon atoms, an alicyclic radical having 3 to 18 carbon atoms, or an aromatic radical having 6 to 26 carbon, wherein the radicals optionally contain one or more oxygen atoms. The $R_{10}$ radical will have a valency equal to "e". As used herein, the term "aromatic" includes, but is not limited to, groups such as phenyl, naphthyl, pyridyl and the like in which the ring may be substituted by groups which do not interfere with the crosslinking reaction such as, but not limited to, $C_1$ to $C_6$ alkyl, nitro, halo, $C_1$ to $C_{12}$ alkoxy and the like. As used herein, the aliphatic and alicyclic groups are optionally substituted by groups which do not interfere with the crosslinking reaction such as, but not limited to, nitro, halo, hydroxy, $C_1$ to $C_{12}$ alkoxy and the like. When "e" is 2, the linear or branched aliphatic radicals preferably have 2 to 14 carbon atoms and the alicyclic radicals preferably have 3 to 12 carbon atoms. When "e" is 3, the linear or branched aliphatic radicals preferably have 3 to 18 carbon atoms and the alicyclic radicals preferably have 4 to 12 carbon atoms. When "e" is 4, the linear or branched aliphatic radicals preferably have 5 to 30 carbon atoms and the alicyclic radicals preferably have 5 to 18 carbon atoms. When "e" is 5, the linear or branched aliphatic radicals preferably have 6 to 30 carbon atoms and the alicyclic radicals preferably have 6 to 18 carbon atoms. When "e" is 6, the linear or branched aliphatic radicals preferably have 8 to 30 carbon atoms and the alicyclic radicals preferably have 8 to 18 carbon atoms.

Examples of polyepoxides for use in the invention include, but are not limited to, ethylene glycol diglycidyl ether, 1,4-cyclohexane dimethanol diglycidyl ether, diglycidyl 1,2-cyclohexane dicarboxylate, N,N-diglycidyl-4-glycidyloxyaniline, and 4,4'-methylenebis(N,N-diglycidylaniline).

The polyepoxides of the invention are readily available or can be prepared by processes known in the art, such as by epoxidation of polyolefin with peracid.

Suitable polyaziridine crosslinkers of the invention include, but are not limited to, those represented by the formula:

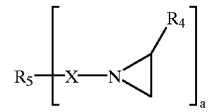

wherein $R_4$ is an alkyl group having 1 to 10 carbon atoms which is optionally substituted by groups which do not interfere with the crosslinking reaction such as, but not limited to, nitro, halo, hydroxy, $C_1$ to $C_{12}$ alkoxy and the like; $R_5$ is an aliphatic radical having 1 to 30 carbon atoms or a direct bond; X is an alkylene group having 1 to 30 carbon atoms, optionally containing an ester group, an ether group, an amide group or a similar inert group; and "a" is 2 to 4. Preferred polyaziridines are those in which $R_4$ is methyl, ethyl, propyl or butyl, X is represented by the formula

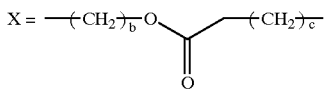

wherein b is 1 to 3 and c is 1 to 3, a is 2 to 3, and $R_5$ is a propylene radical.

Examples of polyaziridines for use in the invention include, but are not limited to, trimethylolpropane tris[(β-N-aziridinyl)propionate], and pentaerythritol tris[(β-N-aziridinyl)propionate].

The polyaziridines of the invention can be prepared by processes known in the art such as by dehydration of α-amino hydroxyl compounds.

Suitable polyoxazoline crosslinkers of the invention include, but are not limited to, those represented by the formula:

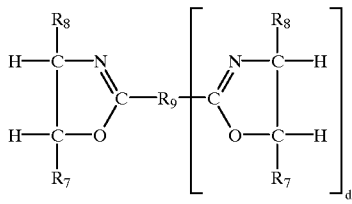

wherein $R_7$ and $R_8$, which may be the same or different, represent hydrogen, an alkyl radical having 1 to 8 carbon atoms or an aryl radical having 6 to 12 carbon atoms; $R_9$ represents a polyfunctional, more particularly difunctional, alkylene radical having 1 to 20 carbon atoms, preferably 1 to 12 carbon atoms, or an arylene radical having 6 to 12 carbon atoms; and d is 1 to 3.

Examples of polyoxazolines for use in the invention include, but are not limited to, ethylenebis(2-oxazoline), 1,2,4-tris(2-oxazoline) butane, and 2,2'-methylenebis[(4S)-4-phenyl-2-oxazoline].

The polyoxazolines of the invention are prepared by processes known in the art.

The crosslinker is preferably used in anhydrous (neat), undiluted, virgin form as a solid or liquid, but alternatively can be a component of a dilute or concentrated solution, dispersion or suspension. A currently preferred crosslinker is ethyleneglycol diglycidyl ether. The amount of crosslinker according to the invention is that amount which is sufficient to crosslink a portion of the acidified or non-acidified aspartate groups of the polyamide precursor corresponding to about 1 to about 30%, preferably about 1 to about 15%, of the S groups in the initial homopolymer PSI. The preferred amount of crosslinker will depend on the specific crosslinker used. The acidified or non-acidified aspartate groups crosslinked during curing comprise from about 1 to about 30%, preferably about 1 to about 15%, of the total succinimide groups originally present in the PSI. This amount and the resulting eventual level of crosslinking renders the polymer superabsorbing in being capable of absorbing from at least 3 times to more than 100 times their weight of water. Though not wishing to be bound to any particular structure, it is believed the crosslinking agent exists as an unreacted component in the uncrosslinked composition which may be intimately admixed with the balance of the components of the composition, or at most is chemically reacted via one functional group of the crosslinker to one carboxylate group of an aspartate group but not to two which would create a crosslink undesirably leading to gel formation.

The crosslinkable, uncrosslinked, partially acidified, hydrolyzed, internally plasticized PSI composition is prepared by i) reacting about 1 to 20% of the succinimide groups of a polysuccinimide polymer having a weight average molecular weight of at least about 20,000 Daltons with one or more monoamines to form an internally plasticized poly(imide-co-amide) intermediate; ii) hydrolyzing essentially all of the succinimide groups of the poly(imide-co-amide) intermediate of i) to form an internally plasticized polyamide; iii) acidifying about 1 to 50% of the hydrolyzed succinimide groups of the polyamide of ii); and iv) admixing crosslinker with the partially acidified, hydrolyzed, internally plasticized polysuccinimide (PSI) composition of iii) under non-crosslinking conditions to form the crosslinkable, uncrosslinked, partially acidified, hydrolyzed, internally plasticized PSI composition.

Another aspect of the invention is a process for forming a partially acidified, hydrolyzed, internally plasticized polyamide which comprises (a) reacting polysuccinimide with about 1 to about 20 mole percent of a monoamine having the formula $HNR_1R_2$ to produce a poly(imide-co-amide); wherein $R_1$ is a hydrogen atom or an alkyl or alkenyl group of 1 to 55 carbon atoms which can be straight chain or branched and unsubstituted or substituted, and $R_2$ is a hydrogen atom, —OH, or an alkyl or alkenyl group of 1 to 55 carbon atoms which can be straight chain or branched and unsubstituted or substituted; wherein the alkyl or alkenyl groups of $R_1$ and $R_2$ optionally contain one or more oxygen atoms; and wherein the optional substituents of the alkyl or alkenyl groups of $R_1$ and $R_2$ are selected from hydroxyl, ether, chloride or ketone; (b) reacting the poly(imide-co-amide) of step (a) with a suitable base to hydrolyze essentially all of the succinimide groups of the poly(imide-co-amide) of step (a) to produce an internally plasticized, hydrolyzed polyamide; and (c) reacting the polyamide of step (b) with a suitable acid to acidify about 1 to 50% of the aspartate groups of the polyamide of step (b). As used herein, about 1 to about 20 mole percent of a monoamine is based on the number of moles of succinimide repeating units in the polysuccinimide, i.e. the mole ratio of monoamine to succinimide repeating units is about 0.01 to about 0.2. In a further embodiment, the partially acidified, hydrolyzed, internally plasticized polyamide of step (c) is contacted with a crosslinker under non-crosslinking conditions to form a partially acidified, hydrolyzed, internally plasticized, crosslinkable polyamide.

At this stage a partially acidified, hydrolyzed, internally plasticized, crosslinkable, uncrosslinked PSI composition exists for contacting with the fiber-containing composition in a manner about to be described which comprises:

i) repeating, internally plasticized structural units represented by formula (3)

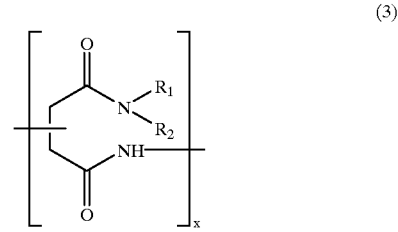

ii) repeating acidified aspartate structural units represented by formula (4)

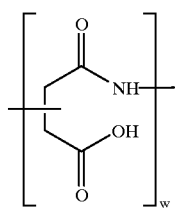

(4)

iii) repeating aspartate structural units represented by formula (5)

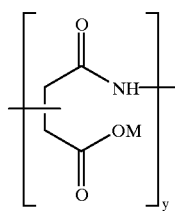

(5)

and iv) crosslinking agent, as described herein, capable under crosslinking reaction conditions of crosslinking units of formula (4), wherein M represents alkali metal, ammonium, quaternary ammonium or mixtures thereof, $R_1$ and $R_2$ are as defined above, and x, w and y represent the mole fractions of structural units (3), (4) and (5) and are respectively about 0.01 to 0.20; about 0.50 to 0.01 and about 0.40 to 0.90 wherein the sum of x, w and y is 1.0. Optionally, the partially acidified, hydrolyzed, internally plasticized, crosslinkable, uncrosslinked PSI contains minor amounts of unreacted succinimide repeating units.

Any conventional method known to those of skill in the art is acceptable for contacting the partially acidified, hydrolyzed, internally plasticized, crosslinkable, uncrosslinked PSI composition with the fiber-containing composition. For example, the solution of partially acidified, hydrolyzed, internally plasticized, crosslinkable, uncrosslinked PSI can be applied by spraying on the fiber-containing composition or by contacting the fiber-containing composition with a bath of the solution of partially acidified, hydrolyzed, internally plasticized, crosslinkable, uncrosslinked PSI. The solution of partially acidified, hydrolyzed, internally plasticized, crosslinkable, uncrosslinked PSI is preferably an aqueous solution for processing reasons.

The at least partially coated fiber-containing composition (which is essentially non-superabsorbing at this stage) is subjected to crosslinking conditions of elevated temperature and time sufficient to cure and crosslink uncrosslinked aspartate groups of the polymer and provide the composition with superabsorbing capability.

Products of the curing step are fiber-containing compositions at least partially coated with partially acidified, hydrolyzed, internally plasticized, crosslinked, superabsorbing polymer derived from polysuccinimide. The crosslinked superabsorbing polymer are formed of polyamide containing at least three divalent or polyvalent moieties randomly distributed along the polymer chain of the following formulas:

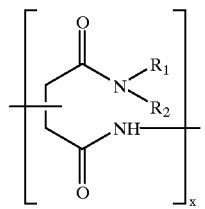

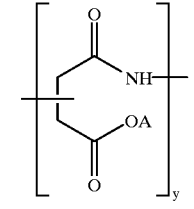

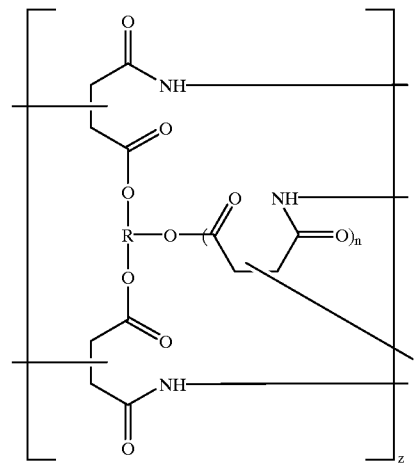

where A represents hydrogen, alkali metal cation, ammonium, quaternary ammonium or mixtures thereof, R represents a divalent or polyvalent crosslinker moiety derived from the crosslinker used, x, y and z represent mole fractions of the moieties in the polyimide and are respectively about 0.01 to 0.20; about 0.40 to 0.90 and about 0.01 to 0.50 wherein the sum of x, y and z is 1.0, and n is an integer from 0 to 4. $R_1$ and $R_2$ are substituents on the monoamine compound used for the internal plasticization of PSI and can be the same or different. Optionally, the superabsorbent polymer contains minor amounts of unreacted succinimide repeating units, i.e. repeating unit disclosed in formula (2) above, and unreacted acidified aspartate repeating units, i.e. repeating unit disclosed in formula (4) above.

The superabsorbent compositions of the invention are useful in the manufacture of moisture absorbent articles, such as disposable diapers, sanitary napkins, incontinence garments, bandages, absorbent liners in meat packing trays, pet tray liners, and the like. The superabsorbent compositions of the invention are particularly useful in the manufacture of thin or ultra-thin disposable diapers which have excellent moisture absorbance capacity, fluid distribution properties and reduced leakage. The superabsorbent compositions of the invention are also useful directly or in non-woven sheet or matting form for agricultural or gardening materials such as water-holding materials for soils, e.g. mixing the superabsorbent compositions directly with soil. The sheet or matting form can also be used for seedlings and landscaping applications.

In making absorbent articles with the superabsorbent composition of the invention, the fiber-containing composition at least partially coated with superabsorbing polymer may be mixed with, attached to, layered in, or dispersed in a porous matrix of fibers. The superabsorbent composition of the invention can be combined with hydrophilic fibers such as cellulose pulp or fluff, cotton liners, and synthetic fibers or a mixture of the fibers and the cellulose fluff. The superabsorbent composition and hydrophilic fibers can be loose or joined as in nonwovens. Suitable synthetic fibers include, but are not limited to, polyesters, copolymers of polyesters and polyamides, polyvinyl alcohol, polypropylene, polyamides, copolymers of isobutylene and maleic anhydride and the like. The synthetic fibers may be meltblown fibers or fibers which have been treated to render them hydrophilic.

Absorbent articles for use in hygienic and sanitary products, such as disposable diapers, are made with a liquid-impermeable backing material, a liquid-permeable bodyside facing material and the liquid-absorbing material sandwiched between the backing material and the facing material. The liquid-impermeable backing material can be made from commercially available polyolefin film and the liquid-permeable facing material can be made from a commercially available nonwoven material, such as spunbonded or corded fibrous web which is wettable and capable of passing the fluid to be absorbed, e.g. urine.

The absorbent articles of the invention may comprise about 5% to about 90% by weight, preferably about 20% to about 70% by weight, of the superabsorbent composition of the invention. In an absorbent article, where the superabsorbent composition of the invention are utilized with other fibers in a matrix, such as a nonwoven material, the superabsorbent composition of the invention is present in an amount from about 30 to about 70 weight percent of the total matrix. In another form of absorbent article, the superabsorbent composition may be present in a containment structure in which the superabsorbent composition of the invention is present in an amount of about 30 to about 90 percent by weight.

The preceding description is for illustration and should not be taken as limiting. Various modifications and alterations will be readily suggested to persons skilled in the art. It is intended, therefore, that the foregoing be considered as exemplary only and that the scope of the invention be ascertained from the following claims.

We claim:

1. A process for preparing a superabsorbing polyamide composition comprising:

i) contacting a dewatered cellulose pulp with a solution of a crosslinkable, uncrosslinked, partially acidified, hydrolyzed, internally plasticized polysuccinimide (PSI) composition to produce an at least partially coated cellulose pulp composition, and ii) drying said at least partially coated cellulose pulp composition under crosslinking conditions to crosslink a portion of uncrosslinked aspartate groups in said PSI composition and form the superabsorbing polyamide composition.

2. The process of claim 1 wherein said PSI composition is an aqueous solution.

3. The process of claim 1 wherein said crosslinkable, uncrosslinked, partially acidified, hydrolyzed, internally plasticized PSI composition of (i) comprises (a) a polymer comprising repeating structural units of

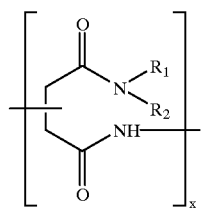

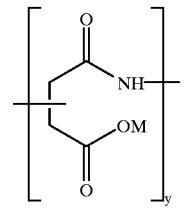

and,

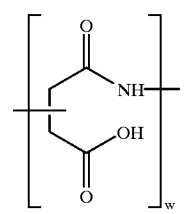

wherein x, y and w represent the molar fractions of repeating structural units of the moieties in the internally plasticized, partially acidified, hydrolyzed, uncrosslinked PSI composition, and are respectively about 0.01 to 0.20, about 0.40 to 0.90 and about 0.01 to 0.50 wherein the sum of x, y and w is 1.0; wherein M is an alkali metal cation, ammonium, quaternary ammonium, or mixtures thereof;

wherein $R_1$ represents a hydrogen atom or an alkyl or alkenyl group of 1 to 55 carbon atoms which can be straight chain or branched and unsubstituted or substituted, and $R_2$ represents a hydrogen atom, —OH, an alkyl or alkenyl group of 1 to 55 carbon atoms which can be straight chain or branched and unsubstituted or substituted; wherein the alkyl or alkenyl groups of $R_1$ and $R_2$ optionally contain one or more oxygen atoms, and are optionally substituted with common organic functional groups not interfering with the hydrolysis reaction; and (b) a crosslinker.

4. The process of claim 3 wherein said crosslinker is selected from polyepoxides, haloepoxides, polyaziridines, polyoxazolines, or mixtures thereof.

5. The process of claim 1 wherein said crosslinkable, uncrosslinked, partially acidified, hydrolyzed, internally plasticized PSI composition is prepared by:

i) reacting about 1 to 20% of the succinimide groups of a polysuccinimide polymer having a weight average molecular weight of at least about 20,000 Daltons with one or more monoamines to form an internally plasticized poly(imide-co-amide) intermediate;

ii) hydrolyzing essentially all of the succinimide groups of the poly(imide-co-amide) intermediate of i) to form an internally plasticized polyamide;

iii) acidifying about 1 to 50l% of the hydrolyzed succinimide groups of the polyamide of ii); and iv) admixing crosslinker with the partially acidified, hydrolyzed, internally plasticized polysuccinimide (PSI) composition of iii) under non-crosslinking conditions to form said crosslinkable, uncrosslinked, partially acidified, hydrolyzed, internally plasticized PSI composition.

6. The process of claim 5 wherein said crosslinker is selected from polyepoxides, haloepoxides, polyaziridines, polyoxazolines, or mixtures thereof.

7. The process of claim 6 wherein the polysuccinimide of i) is prepared by condensation polymerizing L-aspartic acid.

8. The process of claim 1 wherein the aspartate groups crosslinked in step ii) comprise about 1 to about 50% of the total succinimide groups present in the starting PSI.

9. The process of claim 1 wherein said superabsorbing polyamide comprises a polyamide having at least three divalent or polyvalent moieties randomly distributed along the polymer chain having the following formulas:

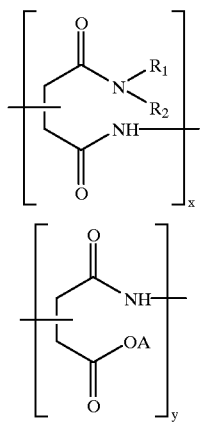

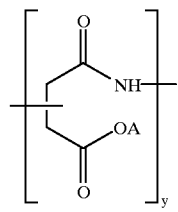

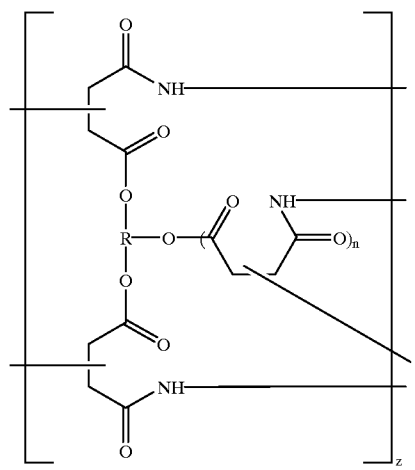

wherein A represents hydrogen, an alkali metal cation, ammonium, quaternary ammonium or mixtures thereof, R represents a divalent or polyvalent crosslinker moiety, x, y and z represent mole fractions of the moieties in the polyamide and are respectively about 0.01 to 0.20; about 0.40 to 0.90 and about 0.01 to 0.50 wherein the sum of x, y and z is 1.0, and n is an integer from 0 to 4; wherein $R_1$ represents a hydrogen atom or an alkyl or alkenyl group of 1 to 55 carbon atoms which can be straight chain or branched and unsubstituted or substituted, and $R_2$ represents a hydrogen atom, —OH, an alkyl or alkenyl group of 1 to 55 carbon atoms which can be straight chain or branched and unsubstituted or substituted; wherein the alkyl or alkenyl groups of $R_1$ and $R_2$ optionally contain one or more oxygen atoms, and are optionally substituted with common organic functional groups selected from hydroxyl, ether, chloride or ketone.

10. A process for preparing a superabsorbing polyamide composition comprising:
i) contacting a fiber-containing composition derived from cellulosic fibers, synthetic fibers or mixtures thereof with a solution of a crosslinkable, uncrosslinked, partially acidified, hydrolyzed, internally plasticized polysuccinimide (PSI) composition to produce an at least partially coated fiber-containing composition, and
ii) heating said at least partially coated fiber-containing composition under crosslinking conditions to crosslink a portion of uncrosslinked aspartate groups in said PSI composition and form the superabsorbing polyamide composition.

11. The process of claim 10 wherein said fiber-containing composition is derived from cellulosic fiber.

12. The process of claim 11 wherein said cellulosic fiber is selected from cellulose pulp, cellulose fluff, cotton fibers or chemically modified cellulose fibers.

13. The process of claim 12 wherein said fiber-containing composition is a nonwoven material.

14. The process of claim 10 wherein said synthetic fibers are selected from polyesters, copolymers of polyesters and polyamides, polyvinyl alcohol, polypropylene, polyamides, copolymers of isobutylene and maleic anhydride or mixtures thereof.

15. The process of claim 10 wherein said fiber-containing material is a nonwoven material.

16. The process of claim 10 wherein said PSI composition is an aqueous solution.

17. The process of claim 10 wherein said crosslinkable, uncrosslinked, partially acidified, hydrolyzed, internally plasticized PSI composition of (i) comprises (a) a polymer comprising repeating structural units of

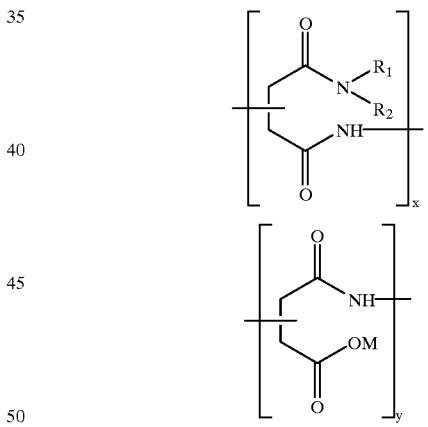

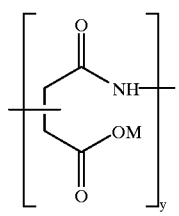

and,

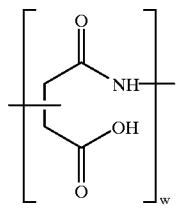

wherein x, y and w represent the molar fractions of repeating structural units of the moieties in the internally plasticized, partially acidified, hydrolyzed, uncrosslinked PSI composition, and are respectively about 0.01 to 0.20, about 0.40 to 0.90 and about 0.01 to 0.50 wherein the sum of x, y and w is 1.0; wherein M is an alkali metal cation, ammonium, quaternary ammonium, or mixtures thereof;

wherein $R_1$ represents a hydrogen atom or an alkyl or alkenyl group of 1 to 55 carbon atoms which can be straight chain or branched and unsubstituted or substituted, and $R_2$ represents a hydrogen atom, —OH, an alkyl or alkenyl group of 1 to 55 carbon atoms which can be straight chain or branched and unsubstituted or substituted; wherein the alkyl or alkenyl groups of $R_1$ and $R_2$ optionally contain one or more oxygen atoms, and are optionally substituted with common organic functional groups not interfering with the hydrolysis reaction; and (b) a crosslinker.

18. The process of claim 17 wherein said crosslinker is selected from polyepoxides, haloepoxides, polyaziridines, polyoxazolines, or mixtures thereof.

19. The process of claim 10 wherein said crosslinkable, uncrosslinked, partially acidified, hydrolyzed, internally plasticized PSI composition is prepared by:

i) reacting about 1 to 20% of the succinimide groups of a polysuccinimide polymer having a weight average molecular weight of at least about 20,000 Daltons with one or more monoamines to form an internally plasticized poly(imide-co-amide) intermediate;

ii) hydrolyzing essentially all of the succinimide groups of the poly(imide-co-amide) intermediate of i) to form an internally plasticized polyamide;

iii) acidifying about 1 to 50% of the hydrolyzed succinimide groups of the polyamide of ii); and iv) admixing crosslinker with the partially acidified, hydrolyzed, internally plasticized polysuccinimide (PSI) composition of iii) under non-crosslinking conditions to form said crosslinkable, uncrosslinked, partially acidified, hydrolyzed, internally plasticized PSI composition.

20. The process of claim 19 wherein said crosslinker is selected from polyepoxides, haloepoxides, polyaziridines, polyoxazolines, or mixtures thereof.

21. The process of claim 20 wherein the polysuccinimide of i) is prepared by condensation polymerizing L-aspartic acid.

22. The process of claim 10 wherein the aspartate groups crosslinked in step ii) comprise about 1 to about 50% of the total succinimide groups present in the starting PSI.

23. The process of claim 10 wherein said superabsorbing polyamide comprises a polyamide having at least three divalent or polyvalent moieties randomly distributed along the polymer chain having the following formulas:

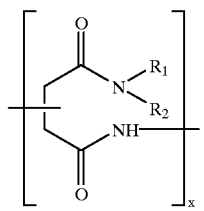

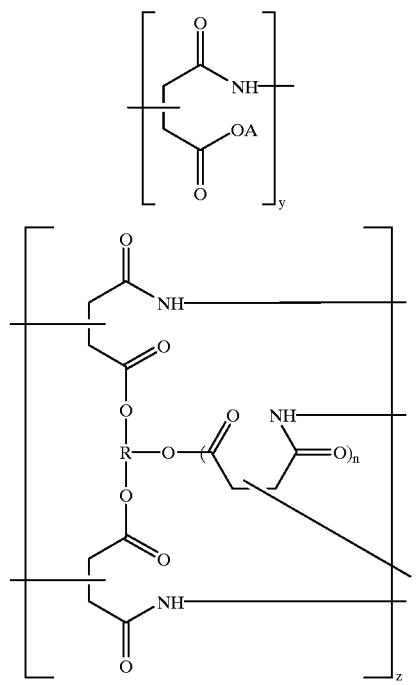

wherein A represents hydrogen, an alkali metal cation, ammonium, quaternary ammonium or mixtures thereof, R represents a divalent or polyvalent crosslinker moiety, x, y and z represent mole fractions of the moieties in the polyamide and are respectively about 0.01 to 0.20; about 0.40 to 0.90 and about 0.01 to 0.50 wherein the sum of x, y and z is 1.0, and n is an integer from 0 to 4; wherein $R_1$ represents a hydrogen atom or an alkyl or alkenyl group of 1 to 55 carbon atoms which can be straight chain or branched and unsubstituted or substituted, and $R_2$ represents a hydrogen atom, —OH, an alkyl or alkenyl group of 1 to 55 carbon atoms which can be straight chain or branched and unsubstituted or substituted; wherein the alkyl or alkenyl groups of $R_1$ and $R_2$ optionally contain one or more oxygen atoms, and are optionally substituted with common organic functional groups selected from hydroxyl, ether, chloride or ketone.

24. A superabsorbing polymer composition comprising a fiber-containing composition derived from cellulosic fibers, synthetic fibers or mixtures thereof which is at least partially coated with a partially acidified, hydrolyzed, internally plasticized, crosslinked, superabsorbing polymer derived from polysuccinimide.

25. The composition of claim 24 wherein said superabsorbing polymer derived from polysuccinimide comprises a polyamide having at least three divalent or polyvalent moieties randomly distributed along the polymer chain having the following formulas:

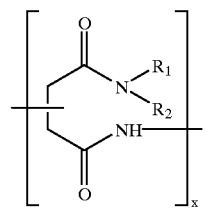

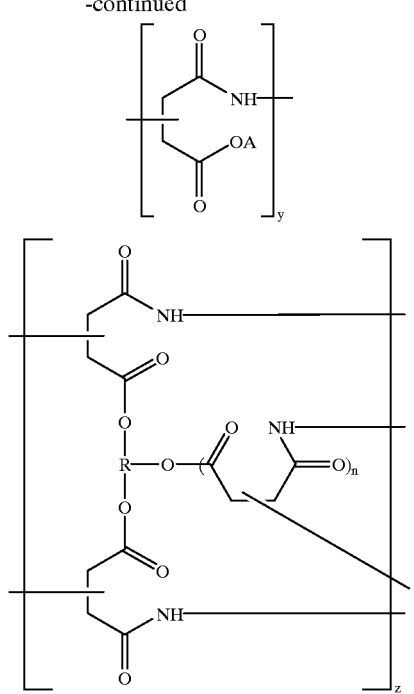

wherein A represents hydrogen, an alkali metal cation, ammonium, quaternary ammonium or mixtures thereof, R represents a divalent or polyvalent crosslinker moiety, x, y and z represent mole fractions of the moieties in the polyamide and are respectively about 0.01 to 0.20; about 0.40 to 0.90 and about 0.01 to 0.50 wherein the sum of x, y and z is 1.0, and n is an integer from 0 to 4; wherein $R_1$ represents a hydrogen atom or an alkyl or alkenyl group of 1 to 55 carbon atoms which can be straight chain or branched and unsubstituted or substituted, and $R_2$ represents a hydrogen atom, —OH, an alkyl or alkenyl group of 1 to 55 carbon atoms which can be straight chain or branched and unsubstituted or substituted; wherein the alkyl or alkenyl groups of $R_1$ and $R_2$ optionally contain one or more oxygen atoms, and are optionally substituted with common organic functional groups selected from hydroxyl, ether, chloride or ketone.

26. The process of claim 25 wherein said fiber-containing composition is derived from cellulosic fiber.

27. The process of claim 26 wherein said cellulosic fiber is selected from cellulose pulp, cellulose fluff, cotton fibers or chemically modified cellulose fibers.

28. The process of claim 27 wherein said fiber-containing composition is a nonwoven material.

29. The process of claim 25 wherein said synthetic fibers are selected from polyesters, copolymers of polyesters and polyamides, polyvinyl alcohol, polypropylene, polyamides, copolymers of isobutylene and maleic anhydride or mixtures thereof.

30. The process of claim 25 wherein said fiber-containing material is a nonwoven material.

31. An absorbent article comprising from about 5 to about 90 percent by weight of a superabsorbent polymer composition according to claim 24.

32. The absorbent article of claim 31 further comprising hydrophilic fibers.

33. The absorbent article of claim 31 wherein the absorbent article is a diaper, sanitary napkin, incontinence garment, bandage, meat packing tray absorbent liner, or pet tray liner.

34. An absorbent composition comprising soil and the superabsorbent polymer composition according to claim 24.

* * * * *

UNITED STATES PATENT AND TRADEMARK OFFICE
CERTIFICATE OF CORRECTION

PATENT NO. : 6,162,541
DATED : December 19, 2000
INVENTOR(S) : Yueting Chou et al Page 1 of 1

It is certified that error appears in the above-identified patent and that said Letters Patent is hereby corrected as shown below:

<u>Column 15,</u>
Line 64, please delete the term "501%" and replace it with the term "50%".

Signed and Sealed this

Tenth Day of July, 2001

Attest:

NICHOLAS P. GODICI
*Attesting Officer*     *Acting Director of the United States Patent and Trademark Office*